United States Patent [19]

Walsh

[11] Patent Number: 4,644,138
[45] Date of Patent: Feb. 17, 1987

[54] TEMPERATURE CONTROL SYSTEM WITH SIMPLIFIED CONTROLLER AND POWER SUPPLY

[75] Inventor: Paul L. Walsh, Elmira, N.Y.

[73] Assignee: Corning Glass Works, Corning, N.Y.

[21] Appl. No.: 488,371

[22] Filed: Apr. 25, 1983

[51] Int. Cl.[4] .............................................. H05B 1/02
[52] U.S. Cl. .................................... 219/501; 219/497; 204/1 T; 323/245; 330/75; 330/103
[58] Field of Search .............. 219/497, 501, 499, 494, 219/508; 204/1 T, 1 R; 323/245; 307/265, 562; 330/75, 86, 110, 103

[56] References Cited

U.S. PATENT DOCUMENTS

| | | | |
|---|---|---|---|
| 3,546,086 | 12/1970 | Sayles | 204/408 |
| 3,928,161 | 12/1975 | McIntyre et al. | 204/428 |
| 4,030,015 | 6/1977 | Herko et al. | 323/288 |
| 4,071,817 | 1/1978 | Bahl | 204/1 S |
| 4,251,342 | 2/1981 | Habdas et al. | 204/427 |
| 4,282,078 | 8/1981 | Chamberland et al. | 204/412 |
| 4,348,577 | 9/1982 | Toyoda et al. | 219/121 PG |
| 4,404,462 | 9/1983 | Murray | 219/497 |
| 4,407,704 | 10/1983 | Mase et al. | 204/1 T |
| 4,500,412 | 2/1985 | Takahashi et al. | 204/425 |
| 4,505,783 | 3/1985 | Mase et al. | 204/1 T |
| 4,505,790 | 3/1985 | Mase et al. | 204/130 |
| 4,505,802 | 3/1985 | Mase et al. | 204/425 |
| 4,505,803 | 3/1985 | Mase et al. | 204/425 |
| 4,505,804 | 3/1985 | Mase et al. | 204/425 |
| 4,505,805 | 3/1985 | Mase et al. | 204/425 |

Primary Examiner—M. H. Paschall
Attorney, Agent, or Firm—R. N. Wardell; J. Jamieson, Jr.

[57] ABSTRACT

The invention includes a simple and inexpensive thermal controller and simple and inexpensive radio frequency alternating current generator which are provided in an improved temperature control system for a resistively heated electrochemical cell. The temperature controller is formed by a single amplifier with feedback circuit which provides the function of a combined deviation amplifier and two mode (percent proportional band and integral functions) controller. The alternating current generator uses a single direct current voltage source to generate a radio frequency alternating electric current. The two elements are combined in a temperature control circuit for a resistively heated electrochemical cell. The control circuit provides an alternating current with varying power by cyclicly shutting the current off for irregular portions of a predetermined cycle period.

14 Claims, 13 Drawing Figures

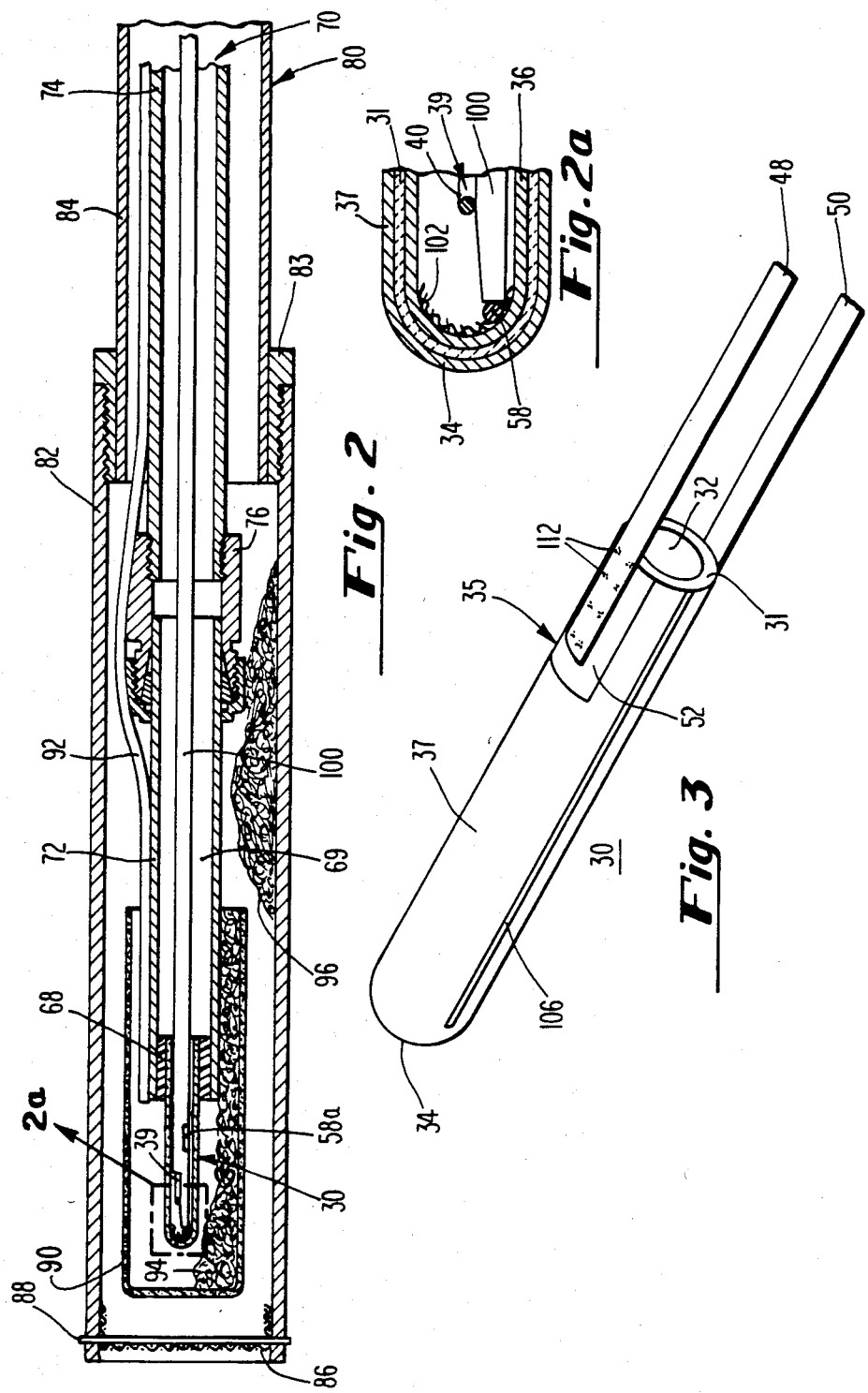

TEMPERATURE CONTROL SYSTEM WITH SIMPLIFIED CONTROLLER AND POWER SUPPLY

FIELD OF THE INVENTION

The invention relates to electrochemical cells operated at elevated temperatures and, in particular, to method and apparatus for heating electrochemical cells such as those used for detecting and/or measuring the concentration of oxygen or other gaseous compounds to an elevated temperature for proper operation.

BACKGROUND OF THE INVENTION

The use of electrochemical cells with solid electrolytic elements and gas porous platinum electrodes for detecting or measuring the content of oxygen or certain other gaseous compounds in a sample gas is well known. See, for example, U.S. Pat. No. 3,928,161 to McIntyre et al. and No. 4,282,078 to Chamberland et al. Materials such as zerconia and yttriathoria and good oxygen ion conductors at elevated temperatures but are less conductive or essentially non-electronically conductive at temperatures between the elevated temperatures and room temperature. Where the electrodes of such a cell are subjected simultaneously to differing oxygen concentrations, an emf is developed across the cell between the electrodes the value of which can be determined by the Nernst equation as follows:

$$emf = \frac{RT}{4F} \ln \frac{P_1(O_2)}{P_2(O_2)} + C.$$

where
 emf = sensor output in volts
 T = absolute temperature
 R = gas constant
 F = Farraday constant
 $P_1(O_2)$ = reference gas (oxygen) partial pressure
 $P_2(O_2)$ = sample gas (oxygen) partial pressure
 C = cell constant Similar equations can be developed for other electrochemical systems. The cell constant C is a correction factor which reflects the inability of a particular cell to perform to theoretical limits represented by the preceding term of the equation. Cells used for oxygen concentration determination should be designed so as to consistently exhibit a known, predetermined cell constant value under all operating conditions in order that the bias in emf might be corrected or, preferably, eliminate such bias entirely (and thus the constant C).

A particularly useful application of oxygen concentration measuring apparatus is for the measurement of the oxygen content of exhaust gases from boilers, furnaces, glass furnaces, etc. in order that the combustion or smelting process may be optimally controlled. Closed loop oxygen sensing systems for combustion control in large steam plants used for power generation or industrial heating have been commercially available for at least ten years. Many of the systems available use a zirconia ($ZrO_2$) based solid electrolyte sensing cell installed in either an in situ or extractive mode. An in situ sensor is physically located within the boiler exhaust gas stream. Extractive systems are located outside the stack and require "plumbing" to carry a representative sample of the flue gas from the stack to the sensor. Currently available commercial units of both designs typically are provided with an auxiliary electric furnace to heat the sensor cell to a satisfactory operating temperature. In in situ sensors, the outer surface of the furnace also typically acts to protect the sensor probe from damage due to the high velocity particles in the flue gas and from dust caking which would effect the accuracy of the sensor.

The auxiliary electric furnaces used by currently available oxygen measuring sytsems have certain undesirable characteristics. They are an added component to the system and represent a significant fraction of its total cost. They are combersome to mount around the electrochemical sensor cell and require considerable design work to assure providing proper heating with simultaneous sample gas exchange. They tend to be bulky and heavy, particularly when used with an in situ sensor which typically extends a meter or more into a flue or stack gas stream. Moreover, such furnaces consume substantial amounts of electrical power, typically between 200 and 400 watts, to maintain a sensor cell at a conventional 800° C. operating temperature. Lastly, they are the least reliable component of the system and are a significant source of repair problems and cost.

Various attempts have been made to eliminate or at least reduce the size and complexity of the auxiliary furnace. For example, U.S. Pat. No. 4,098,650 to Sayles depicts as in situ oxygen measuring device in which the sensing cell is formed with a hollow interior into which is inserted a coil resistance wire heater. The aforesaid U.S. Pat. No. 3,928,161 to McIntyre et al. shows a different configuration for an in situ oxygen detector apparatus incorporating a resistance wire heater located within a tubular member supporting a disk shaped solid electrolyte sensor cell. U.S. Pat. No. 4,334,940 to Habdas et al. depicts yet another solid electrolyte oxygen sensor in which a resistance wire heater is incorporated internally into a tubular support member containing the solid electrolyte sensor cell. While these heater configurations would appear to use less power than auxiliary furnaces, the series resistance windings employed by each would continue to consume significant amounts of electrical power. Moreover, incorporating the heater windings as indicated requres additional manufacturing steps and increasing manufacturing complexity, particularly where the wires are to be threaded through fine holes. Lastly, heating of the said electrolyte sensor cell would appear to be uneven and unpredictable. The sensor output is dependent upon temperature (see the Nernst equation, above) and failure to maintain the sensor at a specific temperature or to accurately measure the temperature of the sensor will lead to errors in the detector output.

OBJECTS OF THE INVENTION

One object of the invention is to provide an improved temperature control system for a resistively heated electrochemical cell.

Another object of the invention is to provide an improved method for resistively heating and operating an electrochemical cell in a gas concentration detecting apparatus.

Another object is to provide a thermal controller of relative simplicity and low cost.

Still another object of the invention is to provide an alternating current generator of relative simplicity and low cost.

SUMMARY OF THE INVENTION

The aforesaid objects and others are satisfied by the subject invention which, in its described preferred embodiment, is used as a closed loop temperature control system for resistively heating an electrochemical cell, typically one used in a gas concentration detecting apparatus.

The temperature control system according to the present invention comprises an alternating electric current generator connected in an electric circuit across at least a portion of the cell by leads and other suitable circuitry. The apparatus includes a thermal controller in the form of an amplifier which generates at an output terminal a control signal having a varying magnitude for varying the power of the alternating current and which receives at an input terminal a compound signal which includes a first component signal related to the difference between an actual temperature of the cell and a desired temperature of the cell and a second component signal related to the control signal outputted by the amplifier. There is further provided a feedback circuit between the output terminal and input terminal of the thermal control amplifier which generates the second component signal. The feedback circuit contains at least two circuit legs connected in parallel, one of the parallel circuit legs having a resistance and the second parallel circuit leg having a capacitance and a resistance in series. The amplifier and feedback circuit form a combination deviation amplifier and two mode (percent proportional band and integral functions) controller. A third parallel leg is preferably provided with a diode allowing current flow between the amplifier output and the amplifier input terminals to improve the reset capability of the capacitance of the resistance-capacitance leg.

The preferred temperature control system further comprises a radio frequency signal generator for generating a radio frequency alternating signal of constant polarity, the signal varying between a minimum voltage level and a maximum voltage level. The alternating current generator converts the radio frequency alternating signal into a radio frequency alternating electric current (i.e. a signal with cyclically varying polarity).

One important aspect of the invention is an alternating current generator formed by a single direct current source which outputs an electric current of substantially constant magnitude and polarity, a capacitance which induces an alternating electric current to flow through a connected circuit and a pair of switches. The two switches alternately charge and discharge the capacitance under the control of the radio frequency alternating signal. In the described embodiment, the first switch is formed by a pair of transistors. A first transistor operates to switch off the second transistor which passes current from the direct current source to the capacitance for charging the capacitor. The second switch is formed by a third transistor also operated by the radio frequency alternating signal to discharge the capacitor when the second transistor is not conducting the direct current.

Another important aspect of the invention is the use of the described temperature control circuit to heat the electrochemical cell of a gas sensing apparatus. According to this aspect of the invention, the radio frequency alternating electric current is generated and passed through at least a portion of the electrochemical cell for resistively heating the cell. The power of the alternating electric current is varied to maintain the cell at a predetermined desired temperature by cyclicly switching the current off for irregular portions of a regular cycle period.

BRIEF DESCRIPTION OF THE DRAWINGS

FIG. 2 is a sectioned view of the apparatus depicting the in situ sensor probe assembly;

FIG. 2a is an expanded view of the probe assembly of FIG. 2 in the area 2a;

FIG. 3 is a view of the preferred embodiment solid electrochemical cell;

DETAILED DESCRIPTION OF THE INVENTION

Preferred Oxygen Detector

Figure 1:
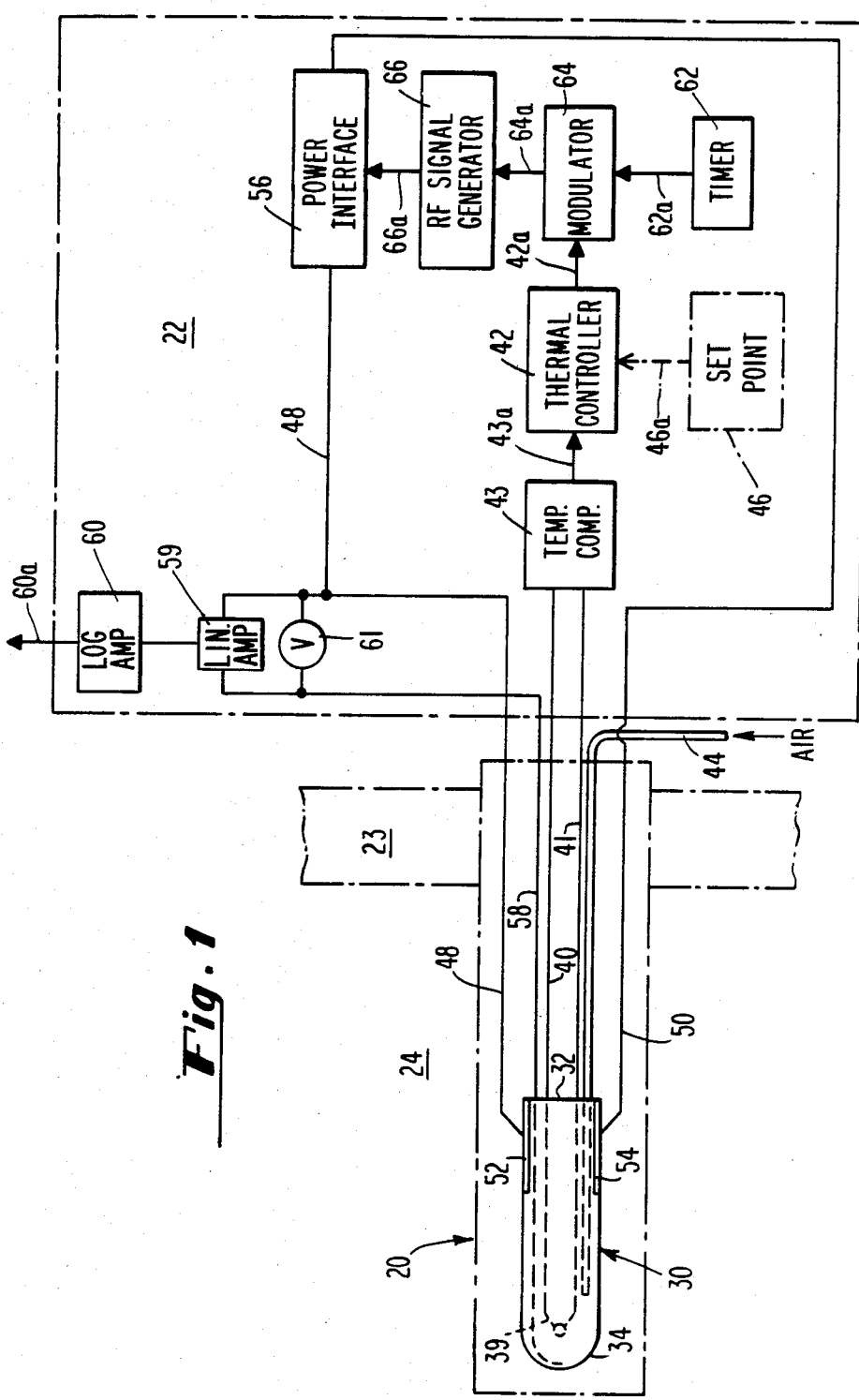
FIG. 1 is a schematic view of the preferred apparatus, in situ oxygen sensor incorporating a solid state electrochemical sensing cell with integral heater/electrode.

FIGS. 1 through 5 and 7 depict the components of the the preferred embodiment of the present invention, a solid state, in situ, low temperature oxygen sensor for monitoring oxygen content in boiler stacks and the like. The apparatus is depicted schematically in FIG. 1 and includes a probe assembly 20, which is depicted in greater detail in FIG. 2 and is inserted through the wall 23 of boiler flue or chimney 24 into the combustion gas stream, and related electronics 22 depicted in greater detail in FIG. 7. The probe assembly 20 includes a tubular electrochemical sensor cell 30 together with protective and supporting elements further described in FIG. 2 to support and protect the electrochemical cell 30 in the flue 24. As is depicted in greater detail in FIGS. 3 through 5, the electrochemical cell 30 includes a solid electrolyte element 31 having a hollow tubular form with an open end 32 and an integral hemispherically formed closed end 34. The electrolyte tube 31 is an yttria (8% by weight) stabilized zirconia substrate fabricated by conventional ceramic forming techniques. As is better seen in FIGS. 4 and 5, an electrically conductive outer electrode layer 37 covers substantially all of the outer surface of the electrolyte element 31. A similar but separate layer 36 is provided on the inner surface of the electrolyte substrate 31 within the hemispherically closed half of the cell.

Returning to FIG. 1, a thermocouple 39 or other suitable temperature sensing device is provided within the electrochemical cell 30 for sensing the electrolyte temperature. Leads 40 and 41 carry an electrical signal generated by the thermocouple 39 to a temperature compensator 43. The compensator 43 develops a voltage level signal passed on line 43a to a thermal controller 42 which controls the heating of the cell 30 by controlling the amount of electrical current circuited through the outer electrode layer 37. The outer electrode layer 37 is used as a sample gas electrode and is exposed to the gases within the flue 24. The inner electrode layer 36 is used as a reference gas electrode and is supplied with ambient (outside) air, having a known concentration (20.95%) of oxygen, by a supply tube 44 or other appropriate means. A pair of pure nickel bus leads 48 and 50 are attached by means of pure platinum foil pads 52 and 54, respectively, to the outer electrode layer 37 and connect the outer electrode layer 37 across a power interface circuit 56. The power interface 56 passes or circuits a radio frequency alternating electric current through the leads 48 and 50, pads 52 and 54, and outer electrode layer 37, thereby resistively heating the outer electrode layer 37 and raising the temperature of the covered solid electrolyte element 31 to an elevated level at which it becomes suitably conductive to oxygen ions. The layer 37, pads 52 and 54, and the portions of the leads 48 and 50 contacting the pads 52 and 54, respectively, together form the integral cell electrode/heater 35 of the subject invention. The inner electrode layer 36 is connected by means of yet another electrical lead 58 in a circuit with the outer electrode layer 37, foil pad 52 and lead 48 across a suitable electrical or electromechanical device for measuring or responding to the emf of the cell 30 developed between the inner and outer electrode layers 36 and 37. For combustion control operations, the emf output of the cell 30 is preferably first amplified by a linear amplifier 59 and then converted to a signal linearly related to oxygen content of the gas in the flue 24 by a logarithmic amplifier 60. The output of the logarithmic amplifier 60 is passed via a line 60a to a conventional closed loop combustion process controller (not depicted), which forms no part of the present invention. Alternatively or in addition, the inner and outer electrode layers 36 and 37 may be circuited across a suitable measuring device such as a high impedance volt meter 61 for a visual indication of oxygen concentration in the gases within the flue 24. The output of the cell 30, measured by the emf developed between the outer electrode layer 37 and inner electrode layer 36, is representative of the difference in oxygen concentration between ambient air and the gases within the flue 24. The apparatus may be configured for operation at a fixed cell temperature or, if desired, the thermal controller 42 may be provided with a set point input from a set point circuit 46 to control the operating temperature of the electrochemical cell. Completing the apparatus in FIG. 1 are a timer circuit 62, a modulator circuit 64 and a radio frequency signal generator 66 which together controllably supply a radio frequency digital signal to the power interface 56 which converts the digitial signal to a similar frequency, low-voltage alternating current.

Operation of the FIG. 1 apparatus is as follows. The yttria stabilized zirconia electrolyte 31 of the sensor cell 30 exhibits an extremely low oxygen ion conductivity until it is heated above a temperature of about 600° C. A voltage difference signal from the thermocouple 39, indicating the maximum temperature of the electrolyte, is passed via leads 40 and 41 to the temperature compensator circuit 43 which compensates the thermocouple signal for the effect of connecting the leads 40 and 41 to the circuit elements 22. The compensated signal is amplified to a magnitude such that it equals the voltage level signal outputted by the set point circuit 46 along line 46a for an equal temperature. The amplified compensated thermocouple voltage level signal is outputted along line 43a to the thermal controller. The thermal controller 42, timer circuit 62 and modulator circuit 64 control the on-off cycling of the radio frequency signal generator 66. As presently embodied, the timer circuit 62 generates a digital timing pulse every 7 milliseconds on line 62a. The modulator circuit 64 responds to the pulse and switches the high frequency signal source 66 on for a fraction of the 7 millisecond period. The radio frequency signal generator 66 can be activated between about 12½% and 97% of the 7 millisecond timing cycle. The duration of a high level signal outputted on the line 64a for activating generator 66 is controlled by the magnitude of the voltage level signal outputted by the thermal controller on line 42a. The radio frequency signal generator 66 outputs on line 66a, in the described embodiment, a 50 kilohertz square wave signal fluctuating between 0 and 15 volts. The square wave signal is converted by suitable circuitry in the power interface circuit 56 to a low voltage level (nominal +6 volts to −6 volts), alternating square wave current of the same frequency. Leads 48 and 50 circuit the high frequency alternating current generated by the power interface circuit 56 through the outer electrode layer 37. It will be appreciated that as the electrolyte 31 exhibits a relatively low electrical conductivity at or below the operating temperature of the sensor 30, which is about 800° C., that there is no flow or at most a negligible flow of alternating current through the electrolyte 31 or inner electrode layer 36 in the preferred embodiment at the indicated voltage levels.

Referring now to FIG. 2, the probe assembly 20 of FIG. 1 is depicted in a side-sectioned view. The major purpose of the probe assembly 20 is to support and extend the electrochemical sensor cell 30 sufficiently far into the stack 24 to obtain a good reading while protecting the cell 30 from abrasive particles in the stack gases and cooling from the stack gas flow. The electrochemical sensor cell 30 is affixed by suitable means such as by a layer 68 of an electrically insulative ceramic cement, within the bore 69 of an extension tube 70. The tube 70 consists of an electrically insulative alumina tube section 72 of a convenient length so as to allow disassembly of the probe assembly 20 and the removal and/or replacement of the cell 30. The alumina tube section 72 is connected to a second extension tube section 74 of stainless steel or other suitable material by a Parker coupling 76 or other suitable means. The cell 30 and extension tube sections 72 and 74 are encased in a protective outer tube 80, formed in the preferred embodiment by lengths of stainless steel tubing 82 and 84 joined by a threaded coupling 83 welded to tube section 84. A wire mesh screen 86 is provided at the open end of the tube 80 to admit stack gases and to retain an insulative material 96, only a portion of which is depicted. The screen 86 is held in position by appropriate means such as pins 88, one of which is depicted in FIG. 2. The present embodiment of the preferred oxygen sensor also presently includes a gas porous ceramic cup 90 surrounding the cell 30 and proximal tip of the alumina extension tube section 72. A hollow tube 92, typically of stainless steel or other suitably heat and corrosion resistant material, is also currently provided with the cup 90 for sensor calibration purposes. The tube 92 carries gas mixtures having a known oxygen content, such as air, to the interior of the thimble 90 and outer electrode layer 37 of the cell 30. In this way, in situ calibration of the apparatus can be accomplished. The space between the thimble 90, sensor 30 and extension tube 72 is filled with an appropriate electrically and thermally insulative material 94 such as alumina silicate only a portion of which is illustrated in FIG. 2 for purposes of clarity. Similarly, the space between the porous ceramic cup 90 and extension tube 70, section tube 72, coupling 76, and metal tube section 74, and the outer stainless steel protective tube 82 is also filled with a gas porous, thermally and electrically insulative material 96, again such as alumina silicate and again only a portion of which is illustrated in FIG. 2 for clarity. The screeen 86, outer insulation 96, porous ceramic cup 90 and inner insulation 94 are all gas porous allowing stack gases to reach the outer electrode layer 37 (see FIGS. 3–5) of the sensor cell 30. These elements also filter solid particulates from the stack gases entering the probe 20.

Inserted into the hollow interior of the cell 30 is a four bore alumina tube 100. Two bores of the tube 100 contain leads 40 and 41 forming the thermocouple 39 which is exposed, as indicated in FIG. 2, at the so-called "active zone" of the sensor 31. That is the location where the solid electrolyte element 31 is heated to its maximum temperature by the outer electrode layer 37 acting as a resistive heater. A third bore of the alimina tube 100 acts as the air supply tube 44 carrying ambient air to the inner electrode layer 36 of the sensor cell 30. The fourth bore of the alumina tube 100 carries the lead 58 contacting the inner electrode layer 36 of the cell 30.

FIG. 2a, an enlarged view of the area 2a of FIG. 2, shows one-half of the thermocouple 39, formed by the lead 40. Chromel-P TM and Alumel TM leads are used for a k-type thermocouple 39 and are joined where exposed from the four bore alumina tube 100. The inner electrode lead 58 has a pure platinum wire tip extending from the tube 100 which is joined within the tube 100 to a pure nickel wire at a point 58a in the vicinity of the junctions between the pure nickel bus leads 48 and 50 and the pure platinum pads 52 and 54, respectively. The purpose is to provide an inner electrode nickel-platinum junction which produces, at the sensor's operating temperature, a compensating emf that is essentially of equal magnitude and opposite polarity to that generated by the junction of the platinum foil pad 52 and nickel lead 48. The purpose is to minimize the magnitude of the cell constant, C, of the apparatus as well as to reduce construction costs of the apparatus. A fine platinum wire mesh 102 is positioned about the tip of the tube 100 so as to be compressed against the inner electrode layer 36 and lead 58 when the tube 100 is inserted into the cell 30. An electrical junction is thus formed between the inner electrode layer 36, platinum mesh 102 and inner electrode lead 58. Leads 48 amd 50 from the outer electrode layer are not depicted in FIG. 2, but are covered, at least in part, by the cement layer 68 and extend down the bore 69 of the tube 70. An electrically insulative covering is provided as the leads 48 and 50 extend from the sensor 30 to prevent shorting or grounding.

While the preferred embodiment is an in situ oxygen sensor, the invention is not limited to in situ sensors or to in situ sensors having the indicated configuration. For example, the sensor 30 is easily adapted to an extractive mode. A sample gas may be supplied to the interior electrode layer 36 or exterior electrode layer 37, with air being supplied to the remaining electrode layer. Alternatively, the configuration of the in situ oxygen sensor 30 may be varied by inverting the orientation of the sensor cell 30 so that the cell 30 extends into and is protected by the alumina tube section 72. This would require modification to the positioning and configuration of the various electrode leads 48, 50, and 58 as well as to the thermocouple 39. In this orientation, the inner electrode layer 36 would be used as the sample gas electrode while the outer electrode layer 37 would be exposed to ambient air and used as the reference gas electrode of the cell 30. Moreover, while an ambient air reference gas electrode is formed in the interior of the preferred embodiment cell 30, it is conceivable that a solid state reference electrode can be formed by using methods and materials known to the art eliminating the need to supply air to the cell 30 interior. See, for example, the solid, oxygen reference electrode revealed in U.S. Pat. No. 3,883,408 to Kim et al., incorporated by reference. It is further envisioned that the present invention may be usefully employed in other areas, particularly in the detection and measurement of other gaseous compounds, apparatus which typically employ similar solid state electrochemical cells 30 utilizing electrolyte and electrode materials selected for the gaseous compound to be detected. See, for example, U.S. Pat. No. 4,282,078 to Chamberland et al., incorporated by reference. It is further believed that at least some inventive aspects of the preferred embodiment oxygen detector apparatus may be usefully employed in the area of oxygen and oxide concentration detection and measurement in fluids, such as molten metals.

Preferred Electrochemical Cell and Integral Electrode/Heater

Figure 4:
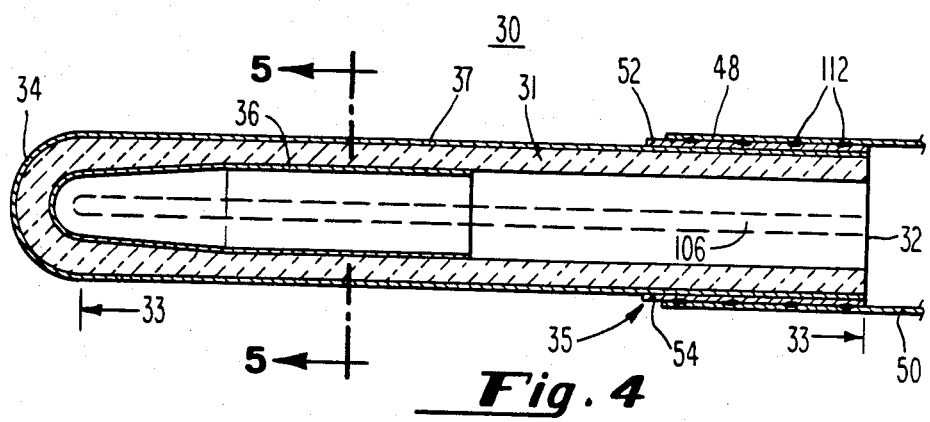
FIG. 4 is a lateral sectioned view of the cell in FIG. 3.
Figure 5:
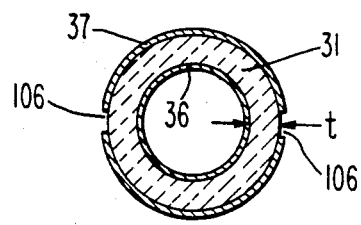
FIG. 5 is a cross-sectional view of the cell of FIG. 3 and FIG. 4 along the lines 5—5.

FIGS. 3–5 depict in greater detail the configuration and construction of the preferred embodiment electrochemical cell 30. The configuration of the cell 30 including the intergral cell electrode/heater 35 comprising the outer electrically conductive, gas porous layer 37, pure platinum lead attachment pads 52 and 54 and the connected portions of pure nickel leads 48 and 50, are significant inventive aspects of the preferred embodiment. The emf developed by the cell 30 is controlled, in part, by the maximum temperature of the electrolyte 31. This is the temperature T of the Nernst equation previously referred to. It has been observed that thermal gradients in the solid electrolyte 31 leading to differing maximum temperatures for the inner and outer electrode layers 36 and 37 cause an offset in the magnitude of the emf actually developed by the cell 30 from that predicted by the Nernst equation. The Nernst equation is only valid where the maximum temperature of the two electrodes are approximately equal. Furthermore, failure to locate and measure maximum temperature generated by the integral electrode/heater can lead to a runaway heating situation. In order to provide a reliable and accurate oxygen measuring apparatus, it is necessary to create an isothermal zone or enlarged area of maximum temperature extending substantially uniformly through and across the electrolyte (i.e., an "active region") between the electrode layers 36 and 37 at a known location. The creation of such a zone allows the temperature to be accurately determined and regulated and thermal gradients between the inner and outer electrodes to be minimized so as to reduce or eliminate a changing and unpredictable cell emf offset.

It has been discovered that the best manner to provide such an isothermal region in the electrolyte is to provide an integral heater/electrode covering a large surface area of the electrolyte 31 with a uniform power density. The preferred design minimizes the length to width ratio of the effective heater/electrode thereby minimizing total electrode resistance while still providing a substantially uniform power density over a large area of the electrolyte. A solid stabilized zirconia electrolyte 31 is provided in the shape of a hollow tubular section 33 and integral, hollow hemispherical section 34. The preferred embodiment sensor uses a partially yttria stabilized zirconia isopressed tubular substrate having a 38 mm overall length, 6 mm outer diameter and maximum inner diameter of 4 mm. The tubular portion 33 of the electrolyte 31 is preferably of a uniform circular cross-section, as is best seen in FIG. 5, and has a substantially uniform cross-sectional thickness, t, at each cross-section. The solid electrolyte tube 31 is formed by conventional ceramic techniques, preferably isopressing for greater dimensional accuracy and more consistent quality. The cross-sectional thickness, t, is substantially the same along most of the length of the tubular portion 33 of the electrolyte 31 but increases near the hemispherical end 34 as a result of the isopressing process. It is desirable to form the electolyte 31 with as substantially a uniform thickness, t, throughout as possible for uniform heating. The preferred integral heater/electrode 35 is formed in part by the layer 37 of an oxygen porous, electrically conductive material applied to all but a pair of narrow diametrically opposing strips 110 of the outer surface of the electrolyte 31. A metallic (preferably platinum) based paste or ink composition is coated as uniformly as possible to the outer surface of the electrolyte 31 so as to form an electrode layer 37 of substantially uniform thickness and uniform electrical resistance. The coating is dried and, if appropriate, heated to sinter the electrode layer material to the electrolyte 31. An ink of the same material having a greater liquid content is used to "cement" the foil pads 52 and 54 to the electrode layer 37. Suitable means such as spot welds 112 are used to affix the leads 48 and 50 to the foil pads 52 and 54, respectively, before attachment of the pads to the electrode layer 37. The inner electrode layer 36 is formed by coating the inner surface of the electrolyte 31 with the same paste or ink.

Figure 6:
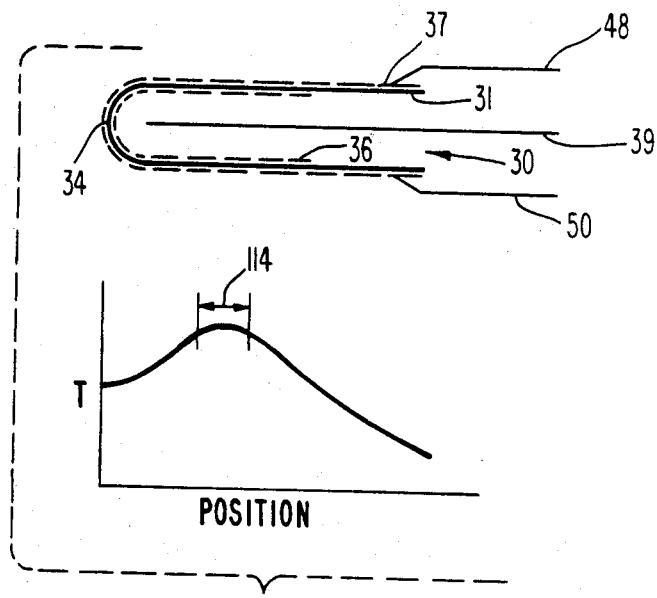
FIG. 6 depicts graphically, the temperature within the cell of FIGS. 3-5 as a function of position from the closed end of the cell.

The outer electrode layer 37, being primarily metallic in all the embodiments being discussed, has a positive temperature coefficient of resistance, as do the metallic foil pads 52 and 54 and leads 48 and 50. Thus, the resistance of the electrode 35 increases with temperature. By employing a substantially uniformly thick outer electrode layer 37, a resistive heater having a substantially uniform power density is formed over the tubular portion 33 of the electrolyte 31. The metallic foil pads 52 and 54 effectively reduce the surface resistivity of the integral heater/electrode 35 near the open end 32 of the electrolyte tube 31. This reduces the electric power density and the resulting generation of heat in the vicinity of the pads 52 and 54. The strips 106 cause the alternating current supplied by the power interface 56 to travel along the length of the layer 37 and over the hemispherical end 34 of the electrolyte 31. At the operating temperature of the sensor 30 (about 800° C.), the outer electrode layer 37 acts as a black body radiator. The rate of heat loss through radiation from the outer electrode layer 37 is greater at the hemispherical end 34 than along the length of the tubular portion 33 of the cell 30. Thus, the resistivity and power density of the electrode layer 37 is effectively reduced at that end 34. Maximum heating therefore occurs in the region between the hemispherical end 34 and the foil pads 52 and 54. FIG. 6 depicts diagrammatically the form of the sensor 30 and the resulting nominal temperature distribution through the electolyte 31 as a function of position along the electrolyte length. In embodiments of the sensor 30 formed from zirconia tubes having an outer diameter of 6 millimeters, an inner diameter of 4 millimeters and a length of approximately 40 millimeters, an "active zone" 114 of maximum temperature having no more than about a 10° C. variation over about a 6 millimeter length of the electrolyte 31 can be generated beginning approximately 9 to 12 millimeters from the hemispherical tip 34.

In the depicted preferred embodiment of the cell 30, the strips 106 extend along the length of the outer surface of the electrolyte 31 from the open end 32 to the hemispherical portion 34. While it is not believed necessary to cover the entire hemispherical portion 34 with the electrode layer 37, as depicted, it is presently suggested to do so as it is believed that covering the entire surface of the hemispherical section 34 with the outer electrode layer 37 reduces heat conduction from the "active zone" to the tip 34 thus minimizing the thermal gradient in the "active zone". It also has the effect of distributing the current density over a broader area preventing the possible generation of hot spots at the ends of the strips 106 where the hemispherical portion 34 meets the tubular portion 33 of the electrolyte body 31. The strips 106 are no wider than is necessary to prevent shorting of the electrode layer 37 at the operating temperature of the sensor 30 and at voltage of the alternating current used to heat the outer electrode layer 37. For the preferred electrode layer material and an yttria stabilized zirconia electrolyte substrate 31 operated at a temperature of about 800° C. with an alternating current voltage fluctuating between about ±6 V, gaps approximately 0.76 millimeters wide in the circumferential direction of the electrolyte 31 were found to be suitable. Gaps 106 should be kept as narrow as possible in the circumferential direction to reduce thermal gradients developing due to electrolyte cooling in the unheated gaps 106.

The area of attachment of the bus strips 48 and 50 to the electrode layer 37 is a potential source of high electrical resistance and therefore of excessive and undesirable heat generation. For this reason and to reduce the overall power requirements of the cell 30, it is suggested that the resistance per unit length of the outer electrode 35 in the region of the intermediate foil pads 52 and 54 and bus strips 48 and 50 be kept to a value less than about 1/10th that in the "active zone". This is substantially achieved by the foil pads 52 and 54 bonded to the outer layer 37. If necessary, it is believed that further reduction in the resistance of the integral heater/electrode 35 can be achieved by overlaying the bus leads 48 and 50 with another layer of similar metal foil. Surface resistivity of the integral heater/electrode 35 and of the electrode layer 37 can be measured by the conventional four probe technique. The surface resistivity measurements reflect a changing resistance in the heater/electrode 35 and layer 37. The surface resistivity of the preferred embodiment platinum-bismuth trioxide electrode material is about 0.05 ohm/square (+50%) or less for a typical 0.001 inch film at room temperature and provides an electrode layer in the preferred apparatus having a total resistance of less than about one-half ohm at room temperature between the first and second nickel lead/platinum foil junctions (48/50 and 49/51). The test may also be used to determine the uniformity of the layer 37 as surface resistivity of the layer 37 is directly proportional to its thickness.

The depicted embodiment of the cell 30 with integral heater/cell electrode 35 is presently preferred for its superior performance given the present fabricating constraints. Other electrode layer application techniques are being studied with may provide a means for controllably varying the thickness of the electrode layer 37. When accomplished, this may allow variation in the construction of the integral heater electrode 35 such as the elimination of the foil pads 50 and 52, the expansion of the active region or the use of even smaller electrolyte shapes.

The proper functioning of the preferred embodiment cell results from the proper balancing of a number of interrelated factors including tube and heater layer size, shape, composition and electrical resistance/conductivity characteristics, sensor operating temperature and heating current voltage. Variation of any parameter may result in some significant portion of the heating current shorting through the electrolyte or the electrolyte and remaining electrode. This will necessarily effect the accuracy of the cell and will probably reduce its operating life.

Models of the preferred embodiment apparatus are presently being fabricated from yttria stabilized (8% by weight) zirconia substrate tubes which are readily available in the size and shape of the solid electrolyte element 31 being employed. However, other suitable oxygen ion conducting solid electrolyte materials such as zirconia stabilized with other compounds and other oxides known in the art may be employed. Indeed, it has been observed that at the operating temperature of the cell 30 of approximately 800° C., that calcia stabilized zirconia is less electronically conductive than the yttria stabilized zirconia, a factor not deemed significant for the preferred embodiment of the cell 30 and integral electrode/heater layer 37, but which may be important in other configurations to prevent a short circuiting of the alternating current through the solid electrolyte 31 during heating. For example, successful operation of a calcia stabilized zirconia electrolyte cell 30 has been demonstrated. At an operating temperature of approximately 800° C., the calcia stabilized zirconia is an order of magnitude less electrically conductive than the yttria stabilized zirconia. However, the calcia stabilized zirconia appears to be more susceptible to electrolytic decomposition from an alternating electronic voltage than does the yttria material. The calcia stabilized electrolyte may be useful in a short operating life application and/or in a different electrode/electrolyte configuration where the reduced electrical conductivity of the calcia stabilized zirconia might prevent undesired shorting of the heater alternating electric current.

Electrode Material

Another inventive aspect of the preferred apparatus is the material employed for the electrode layers 36 and 37. The material has been found to be one of the key components effecting the accuracy, sensitivity and longevity of the sensor. The ideal material used has to be applicable in controllable thickness on the electrolyte 31, form a strong bond (preferably chemical) with the electrolyte to resist spalling or other forms of physical deterioration, have the same thermal coefficient of expansion or otherwise be sufficiently ductile in the thicknesses used to prevent spalling or cracking and have the appropriate electrical resistivity preferably about 0.5 ohms, square/mil or less, again for a typical 0.001 inch thick film. For oxygen concentration sensing with the integral heater/electrode 35, the layer 37 is desirably permeable to gaseous oxygen. Because of its high catalytic activity for the oxygen equilibration reaction, platinum is a preferred oxygen detector electrode material. Nevertheless, platinum cannot be used alone as a heater material because it does not form a chemical bond to the zirconia substrate electrolyte 31 and, if resistively heated, will spall.

Initial experiments were performed using a previously known resistive heater material demonstrating a long-term physical stability with zirconia when heated. When dried, the material essentially comprised two parts by weight powdered platinum, one part by weight powdered gold and a small portion by weight of a glass ceramic frit binder. The material was applied as an ink by brushing or dipping to form a coating approximately 25 microns thick which consolidated to a film approximately 10 microns thick when dried and fired. However, to obtain a one-half ohm resistance desired for the integral heater/electrode 35, thicker films were required. These were formed by coating and then firing successive layers onto the electrolyte 31. The most uniform coating results were obtained by dipping the electrolyte tube into the ink, slowly withdrawing it at a uniform rate and then rotating the tube in a furnace while drying. The particular composition used was a number 2408 Hanovia paste consisting of two parts platinum, one part gold with 3.7% by weight Corning Glass Works #186 BED glass frit to which was added approximately 45% of a proprietary Hanovia liquid medium comprising essentially Texanol. The frit is a lead oxide, titania, silica glass which crystalizes to form $PbTiO_3$ at about 700° C. and which melts at about 1100° C. Three such coatings were applied to the outer and inner surfaces of a zirconia substrate tube. The substrate was dried and fired at approximately 900° C. for one hour after each coating. The electrode layer material was extremely adherent and could not be scraped off with a knife. The lead in the glass frit appeared to react with the gold and platinum to form a low melting temperature alloy chemically bonding the layer to the substrate but also acting as a gaseous oxygen block. The prototype sensor was slow to reach equilibrium and, accordingly, slow to respond to oxygen concentration changes. As other, more promising electrode materials were discovered, further experimentation with the glass frit based material was suspended. However, it is believed that some improvement in the oxygen permeability of the glass frit material might be achieved by a variation of the components. In particular, a reduction in the amount of glass frit used might be made to balance improved integral cell electrode/heater layer oxygen porosity with reduced adherability of the layer to the zirconia substrate. Scoring of the layer also improved oxygen permeability. The glass frit material performed adequately when used as an integral heater/- reference electrode with a conventional platinum layer sensor electrode.

Initial experiments were directed in part to demonstrate that oxygen concentration could be measured using an electrode formed of this material. Although this proved to be true, the search continued for materials providing greater adhesion to the zirconia electrolyte substrate, lower resistivity and, in particular, greater gaseous oxygen permeability for quicker sensor response.

A preferred integral electrode/heater layer material has been discovered possessing these qualities. In addition, the new material is used to provide equal resistivity in thinner layers than the glass frit material thereby reducing costs. The preferred material paste is supplied by Engelhard Industries, Inc. and is prepared by adding to their standard platinum sensor electrode paste, a small amount of bismuth trioxide. The paste is formed from a mixture of dry components comprising a major proportion by weight powdered platinum and a minor proportion by weight bismuth trioxide ($Bi_2O_3$). Trace amounts of gold (0.1–0.5% by weight) and other materials may be present. The dry components are mixed with a suitable liquid vehicle, again such as Texanol, to form a fluid mixture which can be applied to the zirconia substrate electrolyte 31 by a variety of methods. It was found that a coating approximately 0.001 inch thick (about 0.025 mm) provides an electrode layer 37 with an approximately one-half ohm or less total resistance at room temperature which could be heated to an operating temperature of about 800° C. with as little as 15 watts of energy. The paste appears to form a dark residual layer, which may be an alloy, on the substrate after firing. Electron microprobe analysis has shown that the layer forms a chemical bond at the zirconia interface and that the bismuth is concentrated at the interface. Moreover, the material exhibited extremely high gaseous oxygen permeability as indicated by a virtually instantaneous response of test sensors to variations in oxygen concentrations in sample gases employed.

Bismuth trioxide is added in amounts sufficient to improve the adherence or bonding of the resulting electrode layer to the solid electrolyte. It is believed that bismuth trioxide in amounts of up to 10% by weight and preferably between about 1% and 5% by weight may be beneficially employed to form an oxygen porous integral heater/cell electrode layer. The bismuth trioxide appears to act as a flux, as does the gold. Thus, it is believed that the amounts of bismuth trioxide and gold may be varied from the indicated amounts, at least to some extent, without deleterious effect on the characteristics of the resulting layer. It is also suspected, but has not been verified to date, that the bismuth trioxide may be useful in forming electrode layers with base as well as noble metals, where base metals have heretofore been employed in the past. Moreover, the discovered composition may be advantageously employed as a gas electrode material where an integral heater/electrode application is not needed by virtue of its ability to chemically bond the preferred platinum electrode material to a zirconia substrate in an oxygen porous layer.

The preferred paste electrode material is presently being hand applied. A single application provides a layer approximately 0.001 inches (25 microns) thick after firing. Variations in the thickness of the outer electrode layer 37 of the preferred embodiment resulting from these application methods have been observed to produce a variation in surface resistivity of within about ±50% from an average value of about 0.05 ohms/square/mil or less at room temperature. This has proved to provide adequately uniform heating. In this regard, it is believed that the zirconia electrolyte substrate 31 acts as a heat sink diffusing heat rapidly away from hot spots in the electrode layer 37 resulting from uneven layer thickness. Before application of the electrode paste to the outer surface of the electrolyte tube 31, the surface was masked for the slots 106. After each application of the electrode paste, the coated electrolyte substrate was heat-treated at about 980° C.±15° C. for about 15 minutes to sinter the paste. Overfiring appears to reduce the oxygen permeability of the resulting layer. One coat formed the outer layer 37; three coats of the paste were applied to the inner surface of the electrolyte substrate 31 to form the inner electrode layer 36. The coated substrate was heat-treated as previously indicated between each application. Three coats were used to form the inner electrode layer 36 because of the difficulty of applying the paste to the tube interior and the desire to ensure continuity of the inner electrode layer over the inner surface of the electrolyte substrate 31.

Radio Frequency Heating

Other important inventive aspects of the preferred embodiment oxygen sensor and integral heater/electrode cell are the method and apparatus used to resistively heat the cell. It has been observed, in the course of the development of the preferred embodiment apparatus, that the magnitude of the emf developed by the electrochemical cell was effected by the relatively low frequency alternating current (conventional 60 Hz line current) initially used for resistively heating prototype cells. When not influenced by a strong electric or magnetic field, it is believed the oxygen ions in the solid zirconia electrolyte immediately adjacent each electrode layer 36 and 37 will be in equilibrium with the oxygen partial pressure in the gas adjacent the electrode layer 36 and 37 and that the existance of a strong electric or magnetic field will disturb that equilibrium. It was observed that when a steady, low frequency, sinusoidal electric current (i.e., conventional 60 hertz line current) was applied to the heater electrode layer, it was found impossible to simultaneously obtain a meaningful measure of the potential developed between the inner and outer electrodes. A digital type volt meter, which is in essence a periodic sampling instrument, will read out a wide range of potential levels. An analog type volt meter will read out a steady average potential which, however, is far different from the potential which would be produced by that sensor when heated isothermally by a separate heat source such as a conventional auxiliary electric furnace. The shift in the average sensor emf developed due to the low frequency electromagnetic field surrounding the integral heater/electrode is in that direction (i.e., more negative) which is indicative of a lowering of the partial pressure of oxygen adjacent that heater/electrode. On some of the earliest embodiment sensors, the 60 cycle current shifted the average emf by as much as about 225 millivolts. This necessitated following a repetitive heat first then measure cycle in using the early embodiments of the apparatus. It was discovered that as the frequency of the sinusoidal heating current is increased, the average value of the sensor potential shifts in the direction which is indicative of a more correct reading of the oxygen partial pressure at the heater/electrode. Above some sufficiently high frequency, the emf developed by the cell becomes stable and unaffected by the frequency of the heater current.

It has been observed in various embodiments of the subject oxygen sensing apparatus that the permeability of the electrode/heater layer to oxygen has a bearing on the minimum frequency of the heater alternating current that can be employed. The platinum-gold-glass frit material initially employed exhibited a rather poor oxygen permeability. The minimum usable alternating frequency current was in the vicinity of 200 KHz. This is in what is conventionally understood to be the low frequency portion (30–300 KHz) portion of the radio frequency spectrum. It was found that with respect to the preferred platinum-bismuth trioxide electrode/heater layer material, the minimum usable frequency was below 10 KHz which lies within what is generally understood to be the very low frequency portion (3–30 KHz) of the radio frequency spectrum. For ease of coupling between the power source and electrode/heater layer, it has been found preferable to employ a square wave alternating current in a range of about 30 KHz to 100 KHz. As previously indicated, the power interface circuit 56 of the preferred embodiment apparatus generates a 50 KHz square wave alternating current. Higher frequency alternating currents can be employed if power source switching losses are not excessive or interference with radio communication services does not pose a problem. Moreover, a sinusoidal alternating current may be employed in place of a square wave current. There is a significant amount of odd harmonic energy in square wave currents typically generated by existing equipment. Therefore, the fundamental frequency for a square wave current may be somewhat lower than that of a sinusoidal current to have an equivalent end effect on the observed electrochemical cell potential. As the cell developed emf can be made insensitive to the heater current by employing a sufficiently high frequency current, a variety of oxygen concentration apparatus operating methods can be employed. For example, the alternating heater current can be continuously circuited through the integral heater/electrode layer and its amplitude varied in order to provide the required heat input to maintain a stable electrolyte temperature. Alternatively, a constant amplitude alternating current may be switched on and off for variable lengths of time in order to supply the required heat input. In that scheme, which is incorporated into the preferred embodiment apparatus disclosed, the off-time interval is held short enough, for example about 50 milliseconds or less that the transient temperature excursions in the active part of the sensor cell are below the levels which would produce unacceptable variations in the emf developed by the cell.

As an example of the performance capability of the preferred embodiment apparatus, the preferred embodiment electrochemical cell with platinum-bismuth trioxide electrode layers was configured in a heat and measure mode of operation where the instantaneous cell emf was interrogated by a sample and hold read out system immediately prior to the reapplication of each burst of radio frequency heater current. For a change in the off-interval period length from approximately 0.03 to 0.27 seconds, the change in the measured instantaneous potential for one typical experimental cell was in the worst instance 0.7 millivolts. Changing the partial pressure of the oxygen to the inner electrode from a level of 20.95 to 2.79% for cell operating nominal temperature 1073° K., the actual change in instantaneous potential developed by the experimental cell varied from 46.1 to 46.3 millivolts over the above indicated range of off-time interval lengths. According to the Nernst equation, such a concentration change at the indicated temperature should produce a theoretical change in the sensor potential of 46.5 millivolts. Over the same range of off-time interval lengths, the value of the potential observed with an average reading meter was essentially constant at 46.2 to 46.3 millivolts. Without correction, these numbers represent, in the worst case, an error in the determination of partial pressure of oxygen of less than about 2%.

Figure 7:
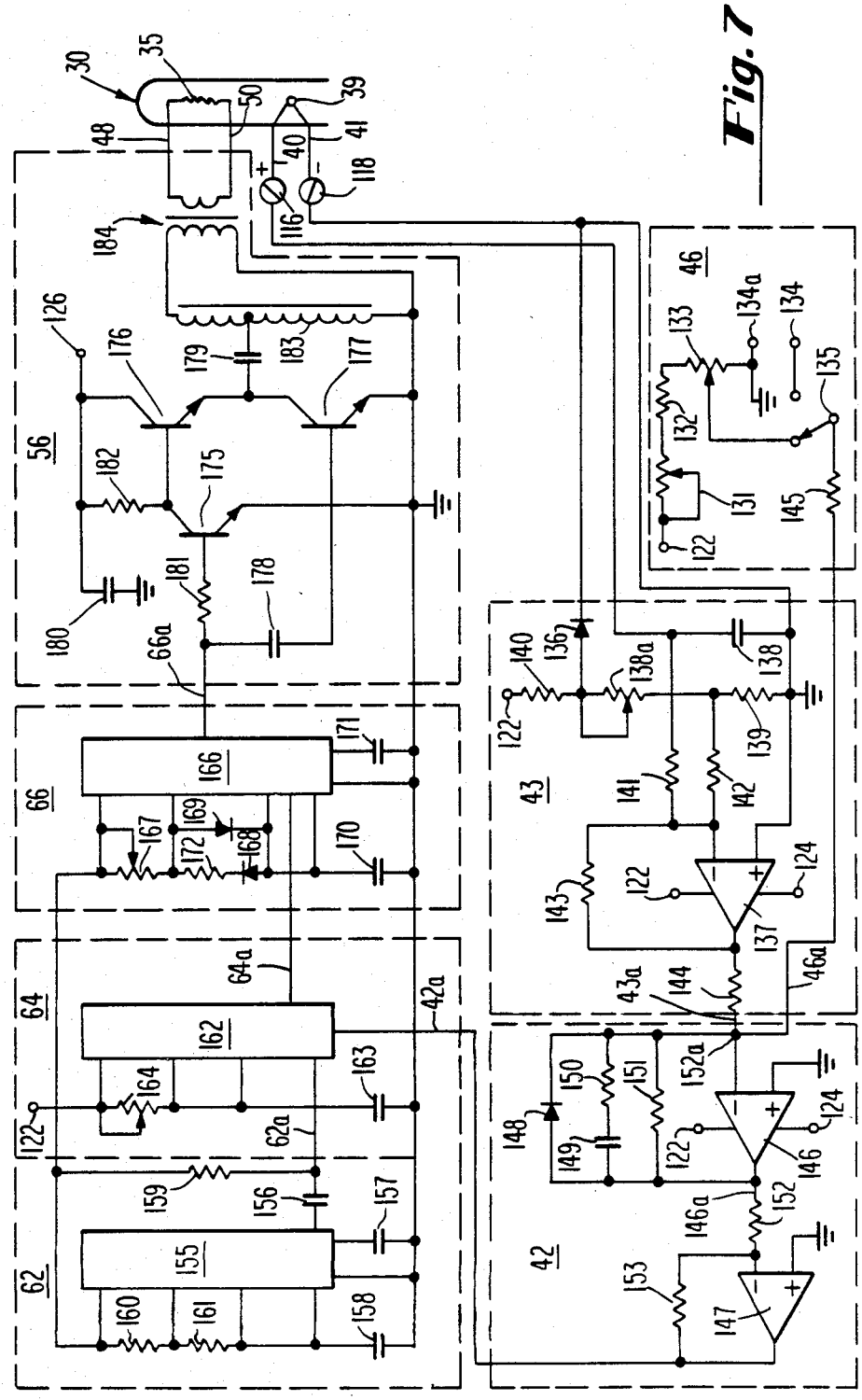
FIG. 7 depicts schematically the electrochemical cell temperature control circuitry of FIG. 1.

Referring now to FIG. 7, there is depicted in greater detail the components of the thermal controller 42, temperature compensator circuit 43, timer circuit 62, modulator circuit 64, high frequency signal source 66 and power interface 56 which together act as a closed loop temperature control circuit for the cell 30. The set point input circuit 46 is optionally provided in order to adjust the operating temperature of the cell 30. A suitable voltage level signal might otherwise be generated by another circuit element to represent a fixed operating temperature for the cell 30. The overall function of the circuit elements 42, 43, 46, 56 and 62 through 66 have been previously described.

As is indicated in FIG. 7, the set point circuit 46 includes a set point calibration circuit formed by a variable resistance 131 and fixed resistance 132. Also included in the circuit 46 are an operator controlled potentiometer 133 with temperature indicating control dial (not depicted) for operator selection of the cell operating temperature, automated set point input junctions 134 and 134a where an externally generated set point voltage signal may be inputted into the set point circuit 46 for automatic temperature control and a manually operated switch 135 for selecting operator or automatic set point control. The circuit 46 generates a voltage level signal passed on line 46a to the thermal controller circuit 42.

Also providing an input to that circuit 42 is the thermocouple temperature compensation circuit 43 which includes a cold junction compensation diode (type IN916) 136, operational amplifier (type OP07) 137, capacitor 138, variable resistor 138a and fixed resistors 139 through 143. Screwheads 116 and 118 represent a circuit junction block to which the thermocouple leads 40 and 41 are connected. The diode 136 is, in reality, located at the junction block so as to be at an identical temperature to that of the negative (Alumel TM) thermocouple lead 41. The operational amplifier 137 accepts at its negative input, the voltage level signal on the positive (Chromel TM) lead 40 of the thermocouple 39 and a temperature compensated voltage level derived from the cold compensation diode 136. These voltage level signals are summed together and amplified so that a compensating voltage due to change in room temperature emf at the termination of the input of the thermocouple 39 is added to the thermocouple signal thus restoring the reverse emf effect caused by connecting the thermocouple leads 40 and 41 to the room temperature junction block. Capacitor 138 is provided to decouple the thermocouple emf from any fluctuating emf component which might be induced in the thermocouple 39 by the alternating heater current. Variable resistor 138a provides means for adjusting the temperature compensation. The remaining resistors provide, with the other elements, an effective gain of 122. The amplified and compensated voltage of the thermocouple 39 is passed on line 43a to the thermal controller 42.

The thermal controller circuit 42 is formed by first and second operational amplifiers (type 347) 146 and 147 with related feedback circuits and resistors 144, 145 and 151 adjusting the gain of signals on lines 43a, 46a and 146a, respectively. The first operational amplifier 146 together with diode 148, capacitor 149 and resistances 150 and 151 form a novel combination deviation amplifier and two mode (percent proportional band and integral functions) controller. The room temperature compensated thermocouple voltage outputted on line 43a is combined with the set point voltage level signal outputted on lines 46a at junction 152 and the combined voltages, together with feedback voltage are fed into the negative input of the first operational amplifier 146. The set point circuit and temperature compensation circuit voltage level signals are scaled for 5 millivolts/° C. The set point voltage level signal is the opposite polarity of that outputted by the compensation circuit amplifier 137 so that the algebraic sum of the output of the compensator circuit 43 and set point circuit 46, as computed by the amplifier 146, is equal to the proportional deviation error selected for optimal temperature control loop stability and desired whole temperature accuracy. The resistors 151 and 144 provide a fixed proportional band error (1%) which represents the allowable percentage difference between the voltage levels on lines 46a and 43a. Reset action occurs as a function of error integration across the capacitor 149. The combination of proportionalizing and reset action is selected to provide, in the preferred embodiment being described, optimal loop stability and whole temperature accuracy within ±1° C. with expected oxygen sensor upsets. Diode 148 is provided to improve the response time of the two mode controller. The diode prevents the output of the amplifier 146 from rising much above zero, as would occur if there were a sudden call for a lower control temperature. The diode 148 reduces the integration requirement imposed on the capacitor 149 under such conditions allowing a faster return to control. The second operational amplifier 147 together with resistors 152 and 153 form a unity gain inverter which reverses the polarity of the output of the first amplifier 146 for driving the modulator circuit 64.

The timer circuit 62 and modulator circuit 64 are formed from a single integrated circuit timer element (type 556) together with related capacitors and resistances. The single integrated circuit timer element is represented functionally by two separate timer elements 155 and 162 in FIG. 7. The timer circuit 62 is formed by the timer element 155 together with capacitors 156, 157, 158 and resistors 159, 160 and 161. Resistor 160 is connected between the first reset and discharge function of the integrated circuit timer while resistor 161 is connected between the first discharge and first threshold functions of the integrated circuit timer. Resistors 160 and 161 define the width (which is arbitrary) of the timing pulse outputted by the timer circuit 62. Capacitor 158 is provided between an input voltage source and the first trigger function of the integrated circuit timer and defines the time period (7 milliseconds in the described embodiment) between consecutive pulses outputted by the timer circuit 62. Capacitor 157 is provided to by-pass the first control voltage function. Resistor 159 and capacitor 156 smooth and shape the signal outputted by the timer circuit 62 on the line 62a.

The output of the timer 62 is passed via the line 62a to the modulator circuit 64 which includes the second timer element 162, capacitor 163 and variable resistor 164. The timer element 162 is formed by suitably wiring (starting from upper left side of 162) the second reset, discharge, threshold, control voltage and output functions of the 556 integrated circuit timer. The capacitor 163 and variable resistor 164 determine the proportion of the 7 millisecond period for the output of the timer element 162 is high on line 64a. The resistor 164 is adjusted to provide for a maximum high output duration of 98% of the 7 millisecond pulse.

The timer element 155 is connected as a free running oscillator. The timer element 162 is connected in a monostable mode so as to be triggered by the negative going edge of each of the consecutive pulses from the timer element 155. The threshold triggering voltage of the timer element 162 is further modulated by the voltage level signal passed from the thermal controller circuit 42 along the line 42a. The timer circuit 162 thus configured acts as a pulse width modulator oscillator. With consecutive pulses being outputted by the timer element 155 at 7 millisecond intervals, the maximum pulse width of the high output level signal outputted by the timer element 162 is adjusted to 6.8 milliseconds by the variable resistor 164 with a threshold voltage of 12.5 supplied from the thermal controller circuit 42. The minimum stable pulse width supplied by the timer element 162 in the depicted configuration is one millisecond with a threshold voltage of 2 from the thermal controller 42. Thus, the total range of effective thermal controller control of the modulator circuit 64 is approximately between 12.5% and 97% of the 7 millisecond duty cycle. The on/off (high/low) voltage level signal outputted by the timer element 162 is passed via line 64a to the radio frequency signal generator circuit 66.

The circuit 66 is formed by an integrated circuit timer 166 (type 555), variable resistor 167, diodes 168 and 169, capacitors 170 and 171 and fixed resistance 172. The timer 166 is also wired as a free running oscillator generating a square wave output signal fluctuating between levels of about 0 and +15 volts at a frequency of 50 Khz. The output of the oscillator 162 is switched on and off by applying the width modulated pulses outputted by the modulator circuit 64 on line 64a to the reset function of the type 555 timer element 166. The frequency of the output of the timer circuit 166 is determined by the combination of capacitor 170 and resistors 167 and 172. The variable resistor 167 is connected between the power input (Vcc) and discharge functions of the 555 timer. The resistor 172 and diodes 168 and 169 are connected between the discharge and threshold functions of the timer while the line 64a feeds into the reset functions. Capacitor 171 by-passes the voltage control function. The variable resistor 167, fixed resistor 172 and diodes 168 and 169 are provided to cause the timer element 166 to generate a symmetrical square wave with equal on and off time periods. Actual adjustment is provided by variable resistor 167. Diodes 168 and 169 provide an alternative discharge path for the voltage charge on capacitor 170 which itself is selected to determine the frequency of the signal (50 Khz) outputted on the line 66a. This assures that the signal generated by the signal generator 66 has an on time of less than or equal to 50% of the duty cycle. This is necessary in order to control symmetric AC heating current through a power interface circuit drive coupling capacitor 179.

The power interface circuit 56 is formed in the preferred embodiment by a novel charge-discharge square wave alternating current signal generator formed by a first transistor (type 2N2218) 175, second and third transistors (type 2N6284) 176 and 177, AC non-polarized capacitors (polyfilm) 178 and 179, electrolytic capacitor 180, and fixed resistor elements 181 and 182. The transistors 175, 176 and 177 form a drive circuit. The transistor 175 is an inverter the purpose of which is to provide a 180° phase inversion of the 50 Khz oscillator signal outputted by the radio frequency signal source 66, along with necessary current amplification to drive the transistor 176. The oscillator 166 drives the transistor 177 through the coupling capacitor 178. The action of driving transistors 176 and 177 alternately cause a direct current to flow through the transistor 176 into capacitor 179 and then to cause another direct current to flow from capacitor 179 through transistor 177 to a common circuit return. Thus, the capacitor 179 is alternately charged by the transistor 176 and discharged through the transistor 177 at a frequency equal to that of the driving frequency (50 Khz) provided by the modulator 66. Capacitor 179 acts like an alternating current generator causing an alternating electric current to flow through the load comprising the transformers 183 and 184. Resistors 181 and 182 adjust the voltages passed to the base and collector, respectively, of transisrtor 175. Capacitor 180 provides a by-pass for a ±45 volt power source fed into the power interface 56 at location 126. The drive coupling capacitor 179 decouples the DC component from the AC current generated by the resistors 176 and 177 causing an alternating square wave current fluctuating between about +20 and −20 volts to be passed to the toroid auto transformer 182. The charge-discharge action of the capacitor 179, unlike the conventional push-pull configuration, requires only one power source supplied at the location 126. The circuit as configured outputs a maximum power of about 30 to 40 watts. The present drive circuit has the advantages of reduced cost, size and improved reliability over more complicated push-pull power circuits and is an improved device where a simple on/off square wave alternating current is needed. The toroid auto transformer 183 steps up the voltage passed to the conventional step-down (isolating toroidal) transformer 184 which, in turn, increases the current passed through the heater circuit 35 of the cell 30 from a level of about 1 amp to about 6 to 7 amps and reduces the voltage accordingly.

The depicted circuit utilizes three power sources: +15 volts denoted by junctions 122, −15 volts denoted by junction 124 and +45 volts denoted by junction 126. The following other circuit elements were used.

| Resistance | Element Resistors |
|---|---|
| 1 ohms | 139 |
| 200 ohms | 138a (maximum) |
| 330 ohms | 182 |
| 1k ohms | 150 & 181 |
| 5k ohms | 131 (maximum) |
| 8.2k ohms | 141, 142 |
| 10k ohms | 133 (potentiometer) 140, 152, & 153 |
| 15k ohms | 159, 172 |
| 18k ohms | 132 |
| 20k ohms | 160 |
| 25k ohms | 167 (maximum) |
| 100k ohms | 144, 145, 161, & 164 (maximum) |
| 1 mega ohm | 143 |
| CAPACITORS | |
| Capacitance | Element |
| 1 microfarad | 178 |
| 10 microfarad | 138 & 179 |
| 100 microfarad | 180 |
| 0.001 farads | 149 & 170 |
| 0.0015 farads | 156 |
| 0.1 farad | 157, 158, 163, & 171 |

Alternate Embodiments

Figure 8:
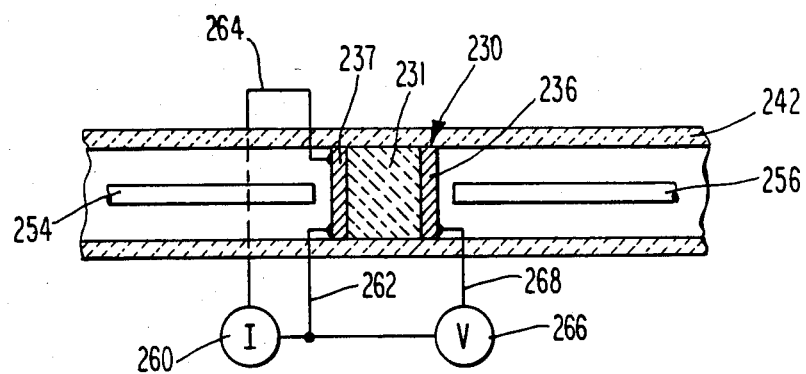
FIG. 8 depicts schematically a second gas detector embodiment incorporating a solid state electrochemical sensing cell with integral heater/electrode and disk shaped solid electrolyte.

While the preferred embodiment of the invention has been described in terms of a low temperature gaseous oxygen detector incorporating a close ended tubular electrochemical sensor cell 30, other sensor cell configurations are envisioned to employ the inventive aspects heretofore described. For example, one common configuration for an oxygen or gaseous oxide detector is depicted schematically in FIG. 8 and comprises a solid state electrochemical cell 230 having a disk shaped solid electrolyte 231, a first gas electrode layer 237 on one outer surface of the electrolyte disk 231 and a second gas electrode layer 236 formed on the opposing outer surface of the electrolyte disk 231. Commonly used in an extractive type detector, suitable means such as a non-conductive alumina tube 272 is used to fixably mount the cell 230 and to seal opposing chambers 250 and 252 in which a sample gas and a reference gas, respectively, are circulated. The gases are brought into the chambers 250 and 252 to the respective electrode layers 237 and 236 by suitable piping such as quartz or alumina tubes 254 and 256. For further information regarding the construction of this type of a sensor, see, for example, the U.S. Pat. No. 4,282,078 to Chamberland et al., incorporated by reference herein. One electrode layer 237 is wired by leads 260 and 262 to an alternating electric current source 260 in order that the layer 237 may be used as an integral cell electrode/heater. In addition, the lead 162 branches into a potentiometer 166 or other suitable high impedance device for responding to emf developed between the two electrode layers 237 and 236. Lead 268 completes the circuit between the electrode layers 237 and 236 through the potentiometer 266. The solid electrolyte wafer 231 is envisioned to have circular outer surfaces upon which the electrode layers 237 and 236 are applied. Electrode patterns which have been devised previously for providing substantially large areas of uniform heating for use as stove elements and the like are described in U.S. Pat. Nos. 3,813,520 and 3,848,111, both to Brouneus and hereby incorporated by reference. It is envisioned that these patterns or simple modifications to them may be employed to provide sufficiently large, essentially isothermal active areas in the cell 230 to allow use of the apparatus as an accurate measuring device. Again, the technology has application both to the detection and measurement of oxygen and to the detection and measurement of other gaseous compounds including various gaseous oxides. Again, a solid reference electrode electrochemically suited for the chemical reaction driving the sensor 230 may be employed in place of the gaseous reference electrode layer 236. Also, the two electrode layers 237 and 236 may be circuited through separate alternating current generators and used as combination heater/electrodes.

Figure 9:
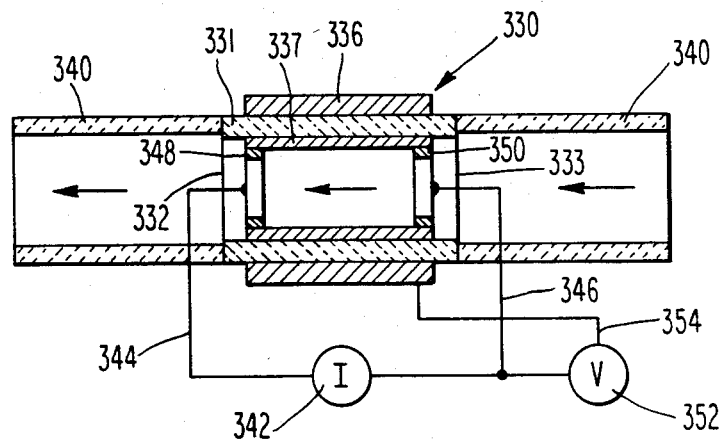
FIG. 9 depicts schematically yet another gas detector apparatus incorporating a solid state electrochemical sensor cell with integral heater/electrode and solid electrolyte with an open tube configuration.

Yet another potential sensor configuration employing an integral heater/electrode which is envisioned is a flow through tube such as is depicted in FIG. 9. An electrochemical sensor cell 330 is provided with a tubular solid electrolyte substrate 331, again of zirconia or other solid electrolyte material suitable for the electrochemical application, having opposing open ends 332 and 333. An inner electrode layer 337 is provided along the inner tubular surface of the substrate 331 while a second electrode layer 336 is applied to the outer surface of the tubular substrate 331. The interior of the tubular substrate 331 would be sealed from its exterior by suitable means such as alumina tubes 338 and 340 circulating a reference gas or sample gas mixture through the interior of the cell 330. The cell 330 is again heated by resistivity heating one or both of the electrode layers 334 or 336. In the depicted embodiment, a high frequency current source 342 is connected by means of bus leads 344 and 346 to circular terminals 348 and 350 at opposing ends 332 and 333 of the inner electrode layer 337. Again, the inner electrode 337 is electrically connected with the outer electrode 336 across a potentiometer 352 or other high impedance circuit for responding to the emf developed by cell 330.

Prototype Apparatus

Figure 10:
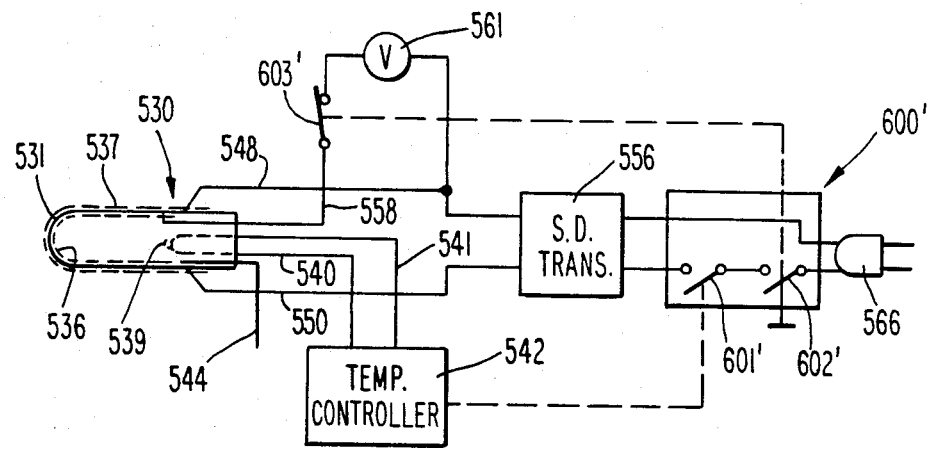
FIG. 10 is a schematic view of a prototype oxygen sensor apparatus.
Figure 11:
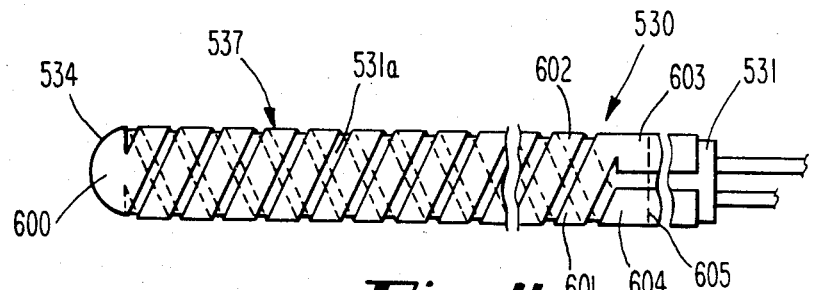
FIG. 11 is a view of a prototype electrochemical cell with integral heater/electrode used in the prototype apparatus of FIG. 10.
Figure 11A:
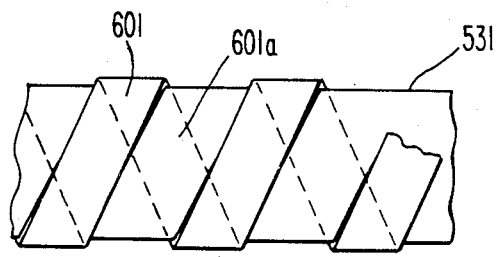
FIG. 11a is an expanded view of a portion of one of two helically wound electrode layer strips forming a part of the integral cell electrode/heater of the prototype cell of FIG. 11.

Depicted diagrammatically in FIG. 10 is an apparatus conceptualizing the manner of operation of the first successful prototype oxygen detection apparatus with integral heater/electrode cell 530. FIGS. 11 and 11a depict the configuration of that prototype cell 530. The apparatus depicted in FIG. 11 includes the sensor cell 530, a thermocouple 539 positioned within the sensor at about the location of the junctions between the leads 548 and 550 and an outer double spiral electrode layer 537 for detecting the maximum temperature of the cell 530. Leads 540 and 541 of the thermocouple 539 are carried to a standard furnace controller 542. A tube 544 carries a sample gas having a known oxygen content to the interior of the cell 530 while the exterior of the cell 530 is exposed ambient air. The atmospheres inside and outside the cell 530 were isolated from one another by suitable means not shown. Leads 548 and 550 connected to step-down transformer 556 across and the integral cell electrode/heater layer 537 on the outer surface of the cell 530. Yet another lead 558 connected an inner electrode layer 536 on the inner surface of the cell 530 and the integral electrode/heater layer 537 on the exterior of the cell 530 across a potentiometer 561. Conventional 60 Hz alternating line current was supplied via plug 556 to the step-down transformer 566. A conceptual switch assembly 600' between the plug 566 and transformer 556 controls the flow of current to the transformer 556. The first switch 601' is operated by the action of the temperature controller 542 while a second switch 602' is manually operated. The operation of switch 602' is linked with that of a switch 603' so that when the alternating current is switched off by switch 602' the potentiometer 561 is activated by switch 603'.

FIG. 11 is a plan view of the prototype electrochemical cell 530. The cell 530 includes a solid yttria stabilized (8% by weight) zirconia substrate solid electrolyte 531 in a tubular configuration similar to that of the solid electrolyte 31 in the cell 30 in FIGS. 1 through 5 having a 6 inch length and ⅜ inch outer diameter. An outer integral cell electrode/heater layer 537 is formed on the exterior surface of the electrolyte 531 and includes a portion 600 covering the hemispherical tip of the electrolyte 531, a pair of opposing, helically extending electrode spirals 601 and 602 about ⅛ inch wide and extending approximately half the length (3 inches) of the tube and ending in opposing parallel strips 603 and 604, respectively, extending longitudinally for the remainder of the tube length (about 3 inches). The leads 548 and 550 are connected to the longitudinally extending parallel strip portions 603 and 604. The helical nature of the strip 601 is depicted in FIG. 11a. The hidden portion of the strip 601 in FIG. 11 being indicated by the phantom element 601a in FIG. 11a. Narrow spirals 531a of exposed electrolyte separated adjoining spirals 601 and 602 of the electrode layer 537. The solid electrode layer 536 of FIG. 10 is provided entirely across the interior surface of the electrolyte 531 extending from the hemispherically closed end 534 of the electrolyte to a point beyond where the longitudinally extending parallel strip portion 603 and 604 begin. The extent of the inner electrode layer 536 of FIG. 10 indicated representatively by the dotted line 605 in FIG. 11.

The operation of the apparatus in FIG. 10 was as follows. Switches 601' and 602' were closed allowing the step-down transformer 556 to supply an alternating voltage with a 60 Hz frequency and amplitude of about 5 to 20 volts. This current was passed via the leads 548 and 550 through the outer electrode layer 537. The outer and inner layers 536 and 537 were each formed by three applications of the aforesaid platinum-gold-glass frit material. The sensor 530 was slowly heated (about 300°–400° C. per hour). The controller 542 monitored the temperature of the cell 530 by means of the thermocouple 539 and controlled the on/off operation of the step-down transformer 556 by the switch 601'. When it was desired to measure the emf developed by the cell 530 across the two electrode layers 536 and 537, the alternating current was switched off manually, such as by the switch 602', and the emf developed between layers 536 and 537 measured (in the depicted apparatus by closing the switch 603'). The apparatus generated a two millivolt emf (cell constant C of the Nernst equation) when ambient air was supplied to both electrodes 536 and 537.

Heating of the cell 530 by the depicted outer electrode layer 537 configuration was less optimal than that of the preferred embodiment outer electrode 37 configuration depicted in FIGS. 2 through 4. It was found that when a voltage of sufficient magnitude to heat the cell 530 was circuited through the platinum-gold-glass frit outer electrode layer 537 at the operating temperature of the sensor (nominally 760° C.) shorting of the heater across the electrolye surface between the helical spiral strip 601 and 602 occurred. Shorting across the electrolyte might occur anywhere along the spiral but once initiated would inevitably travel back toward the junction between the leads 548 and 550 and longitudinally extending parallel strips 603 and 604 of the outer electrode 537 where the voltage difference was greatest. Measurements indicated that when a desired temperature of about 760° C. was eventually produced at the center of the helical windings 601 and 602, the temperature of the electrode at the hemispherical tip 534 was approximately 500° C. and in the vicinity of the junction between the leads 548 and 550 and parallel extending strips 603 and 604 was about 1000° C. Heating of the cell 530 caused the resistivity of the outer electrode layer 537 to rise and the electronic resistivity of the substrate 531 to fall thus forming, in effect, a pair of variable resistors in parallel. The apparatus was made to operate by locating the sensing portion of the thermocouple 539 in the vicinity of the junction between the leads 548 and 550 and the outer electrode layer 537. Once the thermocouple 539 was moved into the vicinity of the junction between the electrode layer 537 and leads 548 and 550 and the voltage adjusted to hold the sensor at about 800° C. and the sensor 530 was successfully operated continually for one week without failure. A 60 Hz alternating current of between about 1.5 and 2.0 amps at about 14 volts was used to heat the apparatus. In another experiment, a calcia stabilized zirconia substrate solid electrolyte was substituted for the yttria stabilized electrolyte 531 in the sensor 530. The calcia stabilized zirconia has an electric conductivity an order of magnitude less than that of the yttria stabilized zirconia at the operating temperatures of the cell 530. The calcia stabilized electrolyte cell provided an active zone about one-half inch long located about one inch back from the tube tip in the spiral region. However, the calcia stabilized zirconia exhibited susceptibility to electrolysis from the alternating (60 Hz) heater current.

Preferred Oxygen Sensor Instrumentation—Temperature Controller

An alternate method of applying a setpoint temperature is by known means of ramping the setpoin linearly at a predetermined rate until the oxygen sensor heater element reaches the desired setpoint temperature. The purpose of this technique is to prevent possible damage to the oxygen sensor heater element or oxygen sensor cell due to too large temperature gradients during heat up of the oxygen sensor device.

While various embodiments of the subject invention has been described and modifications thereto suggested, it will be appreciated that other changes and improvements will be apparent to one skilled in the art. The invention is therefore not limited to the disclosure but is set forth in the appended claims.

What is claimed is:

1. A temperature control system for resistively heating an electrochemical cell comprising:
    current source means for generating an alternating electric current used to resistively heat an electrochemical cell;
    heater circuit means for connecting said current source means in an electric circuit across at least a portion of an electrochemical cell;
    a control amplifier generating at an output terminal a control signal having a varying magnitude for varying the power of said alternating electric current generated by said current source means and circuited through said heater circuit means when said heater circuit means is connected across at least a portion of an electrochemical cell and receiving at an input terminal a compound signal formed from a first component signal related to the difference between an actual temperature of the cell and a desired temperature of the cell and a second component signal related to the control signal outputted by said control amplifier means; and
    a feedback circuit coupled directly between said output terminal and said input terminal containing at least two circuit legs connected in parallel, one parallel circuit leg containing only a resistance and the second parallel circuit leg containing only a capacitance and a resistance in series.

2. The temperature control system of claim 1 wherein said feedback circuit further comprises a third parallel circuit leg with a diode based to allow current to flow from said output terminal to said input terminal.

3. The temperature control system of claim 1 wherein said current source means comprises a signal generator means for generating a radio frequency alternating signal of constant polarity and an alternating current generator means for converting the radio frequency alternating signal into a radio frequency alternating electric current of varying polarity.

4. The temperature control system of claim 3 wherein the alternating current generator means comprises:
    a direct current source outputting an electric current of substantially constant magnitude and polarity;
    capacitance means for inducing an alternating electric current through the heater circuit means and the cell;
    first switch means operated by said radio frequency alternating signal for passing the electric current from said direct current source to said capacitance means when said radio frequency alternating signal is in one of two possible states for charging said capacitance means; and
    second switch means operated by said radio frequency alternating signal for discharging said capacitance means when said radio frequency alternating signal is in the remaining possible state.

5. The temperature control system of claim 3 wherein the alternating current generator means comprises:
    a direct current power source outputting an electric current of substantially constant magnitude and polarity;
    a first transistor having a first collector, a first base and a first emitter, the first collector being connected in a first parallel circuit leg from said direct current power source and the first base receiving said radio frequency alternating signal;
    a second transistor having a second collector, a second base and a second emitter, the second collector being connected in a second parallel circuit leg from said direct current power source and the second base being connected in a third parallel leg from said direct current power source, said first parallel leg and said third parallel leg originating from a common leg parallel with said second parallel leg;
    a third transistor having a third collector, a third base and a third emitter, the third base receiving the radio frequency alternating signal through a capacitor, and the first emitter and the third emitter being connected to ground; and
    a second capacitor between the second emitter and third collector being alternately charged by the second transistor and discharged by the third transistor.

6. The temperature control system of claim 3 further comprising:
    pulse width modulator means between the control amplifier means and the signal generator means for generating a signal cyclically varying between high and low levels, the duration of the high level portion of the signal being regulated by the magnitude of the control signal generated by said control amplifier means.

7. A square wave alternating electric current generator comprising:

signal generator means for generating an alternating signal fluctuating between a high voltage level and a low voltage level of the same polarity;

a direct current source outputting an electric current of substantially constant magnitude and polarity;

first capacitance means for storing an electric charge;

first switch means controlled by said alternating signal for passing the electric current from the direct current source to said first capacitance means to charge said first capacitance means when said alternating signal is in one of the high or low voltage level states;

second switch means controlled by said alternating signal for discharging said first capacitance means when said alternating signal is in the remaining voltage level stage;

said first switch means comprising:

a first transistor having a first collector, a first base and a first emitter, the first collector being connected in a first parallel circuit leg from said direct current power source and the first base receiving said alternating signal; and a second transistor having a second collector, a second base and a second emitter, the second collector being connected in a second parallel circuit leg from said direct current power source and the second base being connected in a third parallel leg from said direct current power source, said first parallel leg and said third parallel leg originating from a common leg parallel with said second parallel leg; and said second switch means comprises:

a third transistor having a third collector, third base and a third emitter, the third base receiving the alternating signal through second capacitance means, the second emitter and third emitter being connected to ground, and the second emitter and third collector being connected to the same side of said first capacitance means.

8. A system for controlling temperature comprising:

oscillator means for generating a first signal alternating between two levels without reversing polarity;

an alternating current generator including a direct current source, a first capacitor, a first switch means between said direct current source and one side of said first capacitor and controlled by said first signal for passing direct current from the direct current source to the one side of the first capacitor to charge the capacitor when the first signal is at one of the two levels and for preventing the flow of direct current from the direct current source to the one side of the first capacitor when the first signal is at the remaining level, and a second switch means controlled by said first signal for discharging said one side of the first capacitor when the first signal is at the remaining level preventing the discharge of said one side of the first capacitor when the first signal is at the one level;

means for generating a second signal related to a temperature to be controlled by the system; and means responsive to said second signal for activating said oscillator means.

9. The temperature control system of claim 8 wherein said first switch means of said alternating current generator comprises:

a first transistor having a first collector, a first base and a first emitter, the first collector being connected in a first circuit leg with the direct current source and the first base receiving said first signal; and a second transistor having a second collector, second base and a second emitter, the second collector being connected in a second circuit leg from said direct current source and the second base being connected in a third circuit leg from said direct current source, said first leg and said third leg originating from a common leg parallel with said second leg and containing a resistance; and said second switch means comprises:

a third transistor having a third collector, a third base and a third emitter, the third base being activated by said first signal;

wherein the first emitter and third emitter are connected to a common current return; and wherein the second emitter and the third collector are connected to the one side of the first capacitor.

10. The system of claim 9 further comprising:

an autotransformer;

a tap from the autotransformer to an opposing side of the first capacitor; and a first circuit loop connecting the autotransformer with a current return.

11. The system of claim 9 wherein said means responsive to said second signal comprises:

controller means for generating a third signal having a value related to the difference between said temperature to be controlled and a predetermined temperature.

12. The system of claim 11 wherein said means responsive to said second signal further comprises:

timing means for outputting a series of timing pulses at a predetermined rate defining equal time periods between said pulses; and modulator means responsive to said timing pulses and to said controller means third signal for activating the oscillator means during each time period in proportion to the magnitude of said controller means third signal.

13. The system of claim 12 wherein said oscillator means is a digital free running oscillator outputting a square-wave signal when activated.

14. The system of claim 13 further comprising:

an autotransformer;

a tap connecting the autotransformer with an opposing side of the first capacitor;

a second, isolating transformer, a first circuit loop connecting the autotransformer in series with one side of the second, isolating transformer; and a second circuit loop including a resistive load connected across a remaining side of the second, isolating transformer, the resistive load being heated by current induced to flow through the second circuit in response to the charge and discharge of the first capacitor.

* * * * *

UNITED STATES PATENT AND TRADEMARK OFFICE
CERTIFICATE OF CORRECTION

PATENT NO. : 4,644,138

DATED : February 17, 1987

INVENTOR(S) : Paul L. Walsh

It is certified that error appears in the above-identified patent and that said Letters Patent is hereby corrected as shown below:

Column 1, line 21, change "zerconia" to --zirconia--.

Column 1, line 21, change "yttriathoria" to --yttria-thoria--.

Column 1, line 21, after "thoria", change "and" (second occurrence) to --are--.

Column 1, line 50, change "preferbly" to --preferably--.

Column 2, line 9, change "sytsems" to --systems--.

Column 2, line 12, change "combersome" to --cumbersome--.

Column 2, line 28, change "as" to --an--.

Column 2, line 44, change "requres" to --requires--.

Column 2, line 47, change "said" to --solid--.

Column 3, line 28, change "is" to --in--.

UNITED STATES PATENT AND TRADEMARK OFFICE
CERTIFICATE OF CORRECTION

PATENT NO. : 4,644,138

DATED : February 17, 1987

INVENTOR(S) : Paul L. Walsh

It is certified that error appears in the above-identified patent and that said Letters Patent is hereby corrected as shown below:

Column 4, line 15, change "laterial" to --lateral--.

Column 5, line 19, change "of" (first occurrence) to --or--.

Column 7, line 35, change "alimina" to --alumina--.

Column 8, line 45, change "intergral" to --integral--.

Column 9, line 51, change "electolyte" to --electrolyte--.

Column 10, line 12, change "electolyte" to --electrolyte--.

Column 11, line 16, change "with" to --which--.

Column 12, line 3, change "thickness" to --thicknesses--.

Column 18, line 21, change "modulator" to --modulated--.

Column 19, line 29, change "$\pm$" to --+--.

Column 21, line 18, change "resistivity" to --resistively--.

UNITED STATES PATENT AND TRADEMARK OFFICE
CERTIFICATE OF CORRECTION

PATENT NO. : 4,644,138

DATED : February 17, 1987

INVENTOR(S) : Paul L. Walsh

It is certified that error appears in the above-identified patent and that said Letters Patent is hereby corrected as shown below:

Column 21, line 46, change "to" to --a--.

Column 21, line 53, after "plug", change "556" to --566--.

Column 21, line 53, after "transformer", change "566" to --556--.

Column 22, line 53, change "electrolye" to --electrolyte--.

Column 23, line 9, delete "and".

Column 23, line 28, change "setpoin" to --setpoint--.

Column 23, line 37, change "has" to --have--.

Column 24, line 5, change "based" to --biased--.

Column 26, line 54, change the second occurrence of "," to --;--.

Signed and Sealed this

Second Day of August, 1988

Attest:

DONALD J. QUIGG

Attesting Officer

Commissioner of Patents and Trademarks